United States Patent [19]
Gentle et al.

[11] Patent Number: 5,492,994
[45] Date of Patent: Feb. 20, 1996

[54] ADHESION ADDITIVES AND CURABLE ORGANOSILOXANE COMPOSITIONS CONTAINING SAME

[75] Inventors: Theresa E. Gentle; Michael A. Lutz, both of Midland, Mich.

[73] Assignee: Dow Corning Corporation, Midland, Mich.

[21] Appl. No.: 371,910

[22] Filed: Jan. 12, 1995

[51] Int. Cl.$^6$ .................................................. C08G 77/08
[52] U.S. Cl. ........................... 528/15; 528/31; 528/32; 556/438; 556/439; 556/440; 556/443; 556/444
[58] Field of Search .................................. 556/438, 439, 556/440, 443, 444; 528/31, 32, 15

[56] References Cited

U.S. PATENT DOCUMENTS

| | | | |
|---|---|---|---|
| 3,529,007 | 9/1970 | Brison et al. | 556/443 |
| 3,772,026 | 11/1973 | Greenwald | 96/77 |
| 3,873,334 | 3/1975 | Lee et al. | 106/287 |
| 3,887,602 | 6/1975 | Thurn et al. | 260/448.2 |
| 4,087,585 | 5/1978 | Schulz | 428/429 |
| 4,196,273 | 4/1980 | Imai et al. | 528/15 |
| 4,329,273 | 5/1982 | Hardman et al. | 524/862 |
| 4,525,400 | 6/1985 | Surprenant | 428/54 |
| 4,631,208 | 12/1986 | Westall | 427/387 |
| 4,658,851 | 4/1987 | Koch et al. | 137/15 |
| 4,719,262 | 1/1988 | Plueddemann | 525/105 |
| 4,721,764 | 1/1988 | Fujiki et al. | 528/15 |
| 4,732,932 | 3/1988 | Waldern | 524/862 |
| 4,786,701 | 11/1988 | Tamaka | 528/15 |
| 4,906,686 | 3/1990 | Suzuki et al. | 524/730 |
| 5,204,437 | 4/1993 | Ikeno et al. | 528/15 |
| 5,232,959 | 8/1993 | Togashi et al. | 523/211 |
| 5,248,751 | 9/1993 | Takahashi et al. | 528/15 |
| 5,371,262 | 12/1994 | Arkles | 556/443 |
| 5,399,651 | 3/1995 | Gentle et al. | 528/15 |

FOREIGN PATENT DOCUMENTS 449181  10/1991  European Pat. Off. .

OTHER PUBLICATIONS

Zeigler et al. *Silicone–Based Polymer Science* pp. 14–16, 1990.

Hardman et al. *Silicones* (reprinted from Encyclopedia of Polymer Science & Engineering) pp. 254–256. 1989.

*Primary Examiner*—David Buttner
*Assistant Examiner*—Margaret Glass
*Attorney, Agent, or Firm*—Robert Spector

[57] ABSTRACT

The novel organosiloxane compounds of the present invention are characterized by the presence of 1) a silicon atom containing at least two alkoxy or other hydrolyzable groups and the group —OR$^1$Si= wherein R$^1$ represents a divalent organic group comprising carbon, hydrogen, and, optionally, oxygen, and 2) a silicon bonded hydrogen atom or alkenyl radical. A preferred method for preparing the compounds is by the reaction of 1) a silane containing a silicon-bonded alkenyloxy group and at least two silicon-bonded hydrolyzable groups or a precursor of said hydrolyzable groups and 2) an organohydrogensiloxane. The reaction is conducted in the presence of a hydrosilation catalyst.

7 Claims, No Drawings

ADHESION ADDITIVES AND CURABLE ORGANOSILOXANE COMPOSITIONS CONTAINING SAME

BACKGROUND OF THE INVENTION

1. Field of the Invention

This invention relates to novel organosilicon compounds. More particularly, this invention relates to novel organosiloxane compounds that impart excellent adhesion to elastomers and gels prepared from organosiloxane compositions that cure by a platinum-catalyzed hydrosilation reaction. The adhesion promoters are particularly effective at relatively low curing temperatures, particularly from ambient up to 70° C.

2. Background Information

A variety of silanes and organosiloxane compounds have been proposed for use as primers and adhesion promoters with organosiloxane compositions that cure by a platinum-catalyzed hydrosilation reaction. These primers and adhesion promoters typically contain two types of reactive groups, one of which is a hydrolyzable group and the second is capable of reacting with either the Substrate to be adhered to or the ingredients of the organosiloxane composition that participate in the curing reaction. For example, the adhesion additives described in U.S. Pat. Nos. 3,772,026 and 3,873,334 are silanes containing acyloxy groups, such as acetoxy, and either a silicon-bonded hydrogen atom or an alkenyl radical. While the acyloxy group exhibits the desired high reactivity in the presence of moisture, the product of this reaction is a corrosive acid.

U.S. Pat. No. 4,196,273 teaches using alkoxysilanes containing ethylenically unsaturated groups, however there is no indication in the examples of this patent that adhesion can be achieved at curing temperatures below 100° C. Using partial hydrolyzates of these silanes as adhesion promoters is described in U.S. Pat. No. 4,329,273. Compositions containing these hydrolyzates did not cure at ambient laboratory temperatures, but did cure at 100° C.

Mixtures of an epoxy-functional alkoxysilane with a liquid silanol-functional polyorganosiloxane containing at least one alkenyl radical are described in U.S. Pat. No. 4,087,585, however there is no indication that compositions containing these adhesion-promoting additives can be cured at temperatures below about 100° C. Adhesion promoting organosilicon compounds containing ethylenically unsaturated, epoxide and alkoxy groups are described in U.S. Pat. No. 4,732,932.

The use as adhesion promoters of organosilicon compounds containing the —COSi(OR')$_3$ group is described in U.S. Pat. Nos. 4,658,851; 4,719,262; and 4,906,686. The adhesion promoters are prepared by the reaction of an alkoxysilane with an ethylenically unsaturated alcohol. U.S. Pat. No. 4,906,686 has the additional requirement that the silane contain an organofunctional group such as epoxy or (meth)acryloxy in addition to alkoxy groups.

The following patents describe organosilanes or organosiloxane compounds containing a silicon-bonded alkenyl radical or silicon-bonded hydrogen atom in addition to silicon-bonded hydrolyzable groups and the use of these compounds as adhesion promoting additives for organosiloxane compositions that cure by a hydrosilation reaction: U.S. Pat. No. 4,786,701; European Patent Application (EPA) No. 449,181; Japanese Laid Open Patent Application No. 4,311,766; U.S. Pat. No. 4,721,764; EPA No. 458,355; and EPA No. 469,890.

A shortcoming of the adhesion promoters described in the preceding paragraphs is the lack of any indication that cohesive bonding of the composition to substrates can be achieved at curing temperatures below about 100° C.

U.S. Pat. No. 3,887,602 describes reaction products of alkoxysilanes containing a silicon-bonded hydrogen atom and allyl ethers of polymerized aldehydes. These reaction products are useful as coupling agents for bonding glass fibers to polymers based on formaldehyde or trioxane. The reaction products can be represented by the formula $(RO)_3Si(CH_2)_3(OCH_2OR')_nOCH_2O(CH_2)_3Si(OR)_3$, where R represents methyl or ethyl, R' is ethylene or n-butylene and the value of n is between 8 and 56.

One objective of this invention is to provide a novel class of organosiloxanes that will cohesively bond organosiloxane compositions to a variety of substrates during curing of the compositions by a platinum group metal catalyzed hydrosilation reaction at temperatures as low as 25° C.

SUMMARY OF THE INVENTION

The novel organosiloxane compounds of the present invention are characterized by the presence of 1) a silicon atom containing at least two alkoxy or other hydrolyzable groups and the —ORSi≡ group wherein R represents an alkylene radical, and 2) a silicon bonded hydrogen atom or alkenyl radical.

DETAILED DESCRIPTION OF THE INVENTION

This invention provides organosiloxane compounds represented by the formula

$$X_mR^2_{(3-m)}SiOR^1[Si(R^3)_3]_n$$

wherein $R^1$ contains at least 3 carbon atoms, exhibits a valence of n+1 wherein n is 1 or 2, and is selected from the group consisting of —$R^4$—, —$R^4OR^5$—, —$R^4OC(O)R^6$— and —$R^7C(O)OR^5$— when n is 1, and $R^1$ is (—$R^4O)_2R^8$— when n is 2 and wherein $R^5$, $R^6$ and $R^8$ are bonded to the oxygen atom in said formula;

$R^4$ represents a hydrocarbylene or substituted hydrocarbylene radical containing at least 3 carbon atoms wherein the substituent is hydroxyl or alkoxy;

$R^5$ is selected from the group consisting of $R^4$ and allyloxy-substituted hydrocarbylene radicals with the proviso that $R^5$ contains at least 2 carbon atoms;

$R^6$ is selected from the same group as R4;

$R^7$ is selected from the group consisting of $R^6$ and a single bond;

$R^8$ represents a trivalent hydrocarbon radical;

each $R^2$ is individually selected from the group consisting of unsubstituted and substituted monovalent hydrocarbon radicals;

each $R^3$ is individually selected from the group consisting of unsubstituted and substituted monovalent hydrocarbon radicals, silicon bonded hydrogen atoms, X and siloxane units represented by the general formula —O[SiR$^9_p$O$_{(3-p/2)}]_q$ wherein q is at least 1 and said siloxane units are sequential when q is greater than 1; with the proviso that at least one substituent represented by $R^3$ contains a silicon-bonded hydrogen atom or alkenyl radical; each $R^9$ is individually selected from the group consisting of X, hydrogen, substituted and unsubstituted monovalent hydrocarbon radicals $X_mR^2_{3-m}SiOR^1$— and —$R^{11}[R^{10}_sSiO_{(3-s)/2}]_r$ wherein r is at least 1 and the siloxane units represented by $R^{10}_sSiO_{(3-s)/2}$ are sequential when r is greater than 1;

each $R^{10}$ is individually selected from the group consisting of monovalent hydrocarbon radicals, hydrogen and X;

$R^{11}$ represents a hydrocarbylene or substituted hydrocarbylene radical containing at least 3 carbon atoms wherein the substituent is hydroxyl or alkoxy; the substituents present on the substituted hydrocarbon radicals represented by $R^2$, $R^3$, $R^9$, $R^{10}$ and $R^{11}$ are selected from the group consisting of halogen, epoxy, amino, mercapto and 3-methacryloxypropyl;

X represents a hydrolyzable group;

m is 2 or 3;

n is 1 or 2;

p is 0, 1, 2 or 3; and s is 0, 1, 2, or 3.

This invention also provides curable organosiloxane compositions comprising

A. a curable polyorganosiloxane;

B. an amount of a curing agent sufficient to cure said composition;

C. an amount of a catalyst sufficient to promote curing of said composition; and D. an adhesion promoting additive of the present invention, wherein said composition cures by a reaction selected from the group consisting of hydrosilation reactions catalyzed by platinum group metals and compounds thereof, the reaction of silicon-bonded hydrogen atoms with silanol groups, the reaction of mercapto groups with one another in the presence of oxygen and a catalyst, the reaction of mercapto groups with alkenyl radicals in the presence of a catalyst, free radical and cationic reactions initiated by irradiation of photosensitive compounds with ultraviolet light, free radical reactions initiated by the thermally induced decomposition of a free radical precursor and reactions initiated by high energy radiation.

The organosiloxane compounds of the present invention can be represented by formula 1.

$$X_mR^2_{(3-m)}SiOR^1[Si(R^3)_3]_n \qquad (1)$$

In formula 1 the substituent identified as $R^1$ is bonded through an oxygen atom to the silicon atom containing the hydrolyzable groups. $R^1$ contains at least three carbon atoms, hydrogen and, optionally, oxygen together with any substituents such as halogen and nitrogen that may be present on the carbon atoms. $R^1$ preferably contains from 3 to 10 carbon atoms and exhibits a valence of two or three. The various alternative embodiments of $R^1$ will be discussed in a subsequent section of this specification.

$R^2$ represents a monovalent hydrocarbon radical. This radical can be unsubstituted or can contain substituents such as halogen atoms, so long as the substituents do not adversely affect the curing or storage stability of organosiloxane compositions containing the present adhesion promoters or the adhesion developed during curing of these compositions. Other substituents that can be present on $R^2$ contribute to the adhesion developed by compositions containing the present compounds as adhesion promoters. These substituents include but are not limited to epoxy, 3-methacryloxypropyl, mercapto and amino, and will be referred to hereinafter and adhesion promoting substituents.

If the present compounds are prepared by a preferred method involving the reaction of 1) a silane containing an ethylenically unsaturated group that is bonded to silicon through an oxygen atom with 2) an organosilicon compound containing at least two silicon-bonded hydrogen atoms, the hydrocarbon radical represented by $R^2$ must be free of ethylenic unsaturation. The reason for this limitation is to avoid formation of undesirable products resulting from the competing reaction of the unsaturated group present on $R^2$, rather than the desired ethylenically unsaturated group, with silicon-bonded hydrogen atoms.

The monovalent silicon-bonded hydrocarbon radicals other than alkenyl that are present in the compositions of this invention contain from 1 to 20 or more carbon atoms, and can be alkyl such as methyl, ethyl or propyl, cycloalkyl such as cyclohexyl, aryl such as phenyl, alkaryl such as tolyl or xylyl and aralkyl such as benzyl. The substituents that can be present on these hydrocarbon radicals include but are not limited to halogens such as fluorine and chlorine and any of the adhesion promoting substituents defined in a preceding section of this specification. The hydrocarbon radicals present on the various silicon atoms can be identical or different. These hydrocarbon radicals are preferably methyl, ethyl, 3,3,3-trifluoropropyl or phenyl, this preference being based on the starting materials, typically the corresponding chlorosilanes, used to prepare the present organosilicon compounds. At least one of the radicals present on any silicon atom is preferably methyl.

Each of substituents identified as $R^3$ is individually selected from monovalent hydrocarbon radicals that can be unsubstituted or substituted, silicon-bonded hydrolyzable groups represented by X and the group $O[SiR^9_pO_{(3-p)/2}]_q$ where p is 0, 1, 2, or 3 and q is at least 1.

It should be apparent that the identity of each of the three substituents identified as $R^3$ will depend upon the reactants used to prepare the present compositions. In accordance with a preferred method for preparing the compositions, a silane corresponding to the general formula $X_mSiR^2_{3-m}OR^{1'}$ is reacted with an organohydrogensiloxane containing at least two silicon-bonded hydrogen atoms. In this formula $R^{1'}$ represents an ethylenically unsaturated precursor of the group represented by $R^1$. For example, when $R^1$ is n-propylene $R^{1'}$ is allyl.

In accordance with this method for preparing the present compounds, the group $[Si(R^3)_3]$ in formula 1 represents the residue of the organohydrogensiloxane remaining following removal of the silicon-bonded hydrogen atom involved in the reaction with the silane. Each of the groups represented by $R^3$ can be an unsubstituted or substituted monovalent hydrocarbon radical, a hydrogen atom or at least one siloxane unit represented by the formula $SiR^9_pO_{(3-p)/2}$.

Using the preferred preparative method at least one of the groups represented by $R^3$ is $O[SiR^9_pO_{(3-p)/2}]_q$ and at least one of the $R^9$ substituents in one of the siloxane units is a silicon-bonded hydrogen atom.

When the reaction product of the alkenyloxy-substituted silane, referred to herein as reactant D1, and the organohydrogensiloxane, referred to herein as reactant D2, is not further reacted, each of the substituents represented by $R^9$ is individually selected from a hydrogen atom and unsubstituted or substituted monovalent hydrocarbon radicals. When $R^9$ represents a hydrocarbon radical it is preferably an alkyl radical containing from 1 to 4 carbon atoms, phenyl or 3,3,3-trifluoropropyl. When more than one $R^9$ radical on a silicon atom represents a hydrocarbon radical, at least one of these hydrocarbon radicals is methyl.

One embodiment of the present compounds can be prepared by reacting the reaction product of reactants D1 and D2 with a diene type of hydrocarbon containing two carbon-carbon double bonds, such as butadiene. In the embodiment at least one of the $R^9$ substituents in one of the units represents an alkenyl radical. This alkenyl radical preferably contains from 2 to 6 carbon atoms, and is terminally unsaturated.

X in formula 1 represents a silicon-bonded hydrolyzable group. Groups of this type include but are not limited to alkoxy, carboxy, ketoximo, amino, amido and aminoxy. When the adhesion promoting additives are incorporated into compositions that cure by a hydrosilation reaction, alkoxy and ketoximo groups are preferred, based on the known tendency of nitrogen compounds to inhibit the platinum group metal containing catalysts that are typically used as catalysts for these reactions. X is preferably an alkoxy group containing from 1 to about 4 atoms, based on the volatility of the corresponding alcohols, which are formed as by-products during preparation of the present compounds.

In formula 1 m is 2 or 3, preferably 3.

In accordance with the preferred method for preparing the present compounds the bond between $R^1$ and the adjacent silicon atom shown in formula 1 is formed by the reaction of 1) a silane containing one or two ethylenically unsaturated substituents and two or three hydrolyzable groups with 2) an organosilicon compound containing at least two silicon-bonded hydrogen atoms. Classes of silanes that can be reacted with compounds containing at least two silicon-bonded hydrogen atoms to obtain ingredient D of the present compositions are described in U.S. Pat. No. 4,719,262, which issued to Edwin Plueddemann on Jan. 12, 1988. These silanes will be referred to hereinafter as reactant D1. This entire patent is incorporated into the present specification by reference as a teaching of compounds useful as reactant D1. The terminally unsaturated organosilicon compounds described in this patent can be prepared by reacting one of five classes of organic compounds with a silane containing at least three silicon bonded hydrolyzable groups.

The five classes of organic compounds that can be reacted with a silane containing at least three hydrolyzable groups to form compound D1 are 1) terminally unsaturated alcohols, 2) ethers derived from the reaction of an alcohol of this type with either a saturated polyhydric alcohol or a polyhydric phenol, 3) esters derived from the reaction of a terminally unsaturated alcohol with a saturated hydroxyl-substituted carboxylic acid; 4) esters derived from an ethylenically unsaturated carboxylic acid with a saturated alcohol containing at least two hydroxyl groups and 5) ethers derived from an ethylenically unsaturated monohydric alcohol and an alcohol containing at least 3 hydroxyl groups.

Typically one mole of the ethylenically unsaturated hydroxyl-substituted organic compound used to prepare reactant D1 is reacted with each mole of a silane containing at least three hydrolyzable groups per molecule and represented by the formula $X_{m+1}R^2_{3-m}Si$, wherein m is 2 or 3.

In the embodiment of ingredient D wherein $R^1$ is an alkylene radical represented by $R^4$ reactant D1 exhibits the formula $CH_2=C(R^{12})R^{4'}OSiX_mR^2_{(3-m)}$, $R^{4'}$ represents an alkylene radical, and the group $—CH_2CH(R^{12})R^{4'}—$ constitutes $R^4$. In this embodiment, referred to as I, $CH_2=C(R^{12})R^{4'}O—$ represents the residue remaining following removal of the hydrogen atom from the hydroxyl group of a terminally unsaturated alcohol, and $R^{12}$ represents a hydrogen atom or a monovalent hydrocarbon radical. As used in this specification the term "terminally unsaturated" implies the presence of a hydrocarbon radical that includes a $CH_2=C(R^{12})—$ group.

Terminally unsaturated monohydric alcohols useful for preparing embodiment I of reactant D1 contain from 3 to 20 or more carbon atoms, and include but are not limited to 3-buten-1-ol, 3-buten-2-ol, 2-methyl-3-buten-2-ol, 5-hexen-1-ol, 9-decylen-1-ol, 10-undecylen-1-ol, 17-octadecylen-1-ol and the isomeric allyl substituted cyclohexanols. Preferred alcohols contain from 3 to 12 carbon atoms.

Terminally unsaturated polyhydric alcohols or partial ethers thereof can be substituted for the monohydric alcohol.

A second embodiment of reactant D1, referred to hereinafter as II, is one wherein the ethylenically unsaturated group present in reactant D1 exhibits the general formula $CH_2=C(R^{12})R^{4'}OR^5O—$ and the group represented by $R^1$ exhibits the formula $—CH_2CH(R^{12})R^{4'}OR^5—$. The radicals represented by $R^{4'}$ and $R^{12}$ are defined in the preceding paragraphs and $R^5$ represents a hydrocarbylene or substituted hydrocarbylene radical.

In embodiment II, the ethylenically unsaturated group represents the residue remaining following removal of the hydrogen from a free hydroxyl group of the saturated polyhydric alcohol portion of an ether derived from that alcohol and a terminally unsaturated alcohol containing at least one hydroxyl group. The unsaturated alcohol is preferably monohydric.

The saturated polyhydric alcohol is preferably dihydric and can be represented by the formula $HOR^5OH$. Preferably $R^5$ represents unsubstituted alkylene, hydroxyalkylene, cycloalkylene or phenylene, this preference being based on the availability of the corresponding alcohols. Suitable saturated polyhydric alcohols include but are not limited to ethylene glycol, the isomeric propylene glycols, glycerol, 1,1,1-trimethylolpropane, 1,4-cyclohexanediol and other alcohols containing at least two hydroxyl groups per molecule and up to 20 or more carbon atoms. $R^5$ preferably contains from 2 to 12 carbon atoms.

Partially etherified polyhydric alcohols containing three or more hydroxyl groups, at least two of which are unreacted, are also suitable precursors for the alcohol portion of compounds corresponding to embodiment II.

Suitable terminally unsaturated alcohols include those discussed in connection with embodiment I of reactant D1 in addition to allyl alcohol.

In a third embodiment of reactant D1 the ethylenically unsaturated group exhibits the formula $CH_2=C(R^{12})R^{4'}OC(O)R^6O—$ and the $R^1$ group in ingredient D exhibits the formula $—CH_2C(H)(R^{12})R^{4'}OC(O)R^6—$. $R^{4'}$ and $R^{12}$ are as previously defined, $R^6$ is selected from the same group as $R^4$ and the $—CH_2C(H)(R^{12})R^{4'}—$ divalent group constitutes $R^4$. This divalent group is derived from the ester of an unsaturated monohydric alcohol and a saturated hydroxycarboxylic acid. $R^4$ and $R^6$ preferably contain from 3 to 12 carbon atoms.

In a fourth embodiment (IV) of reactant D1 the ethylenically unsaturated group exhibits the formula $CH_2=C(R^{12})R^{7'}C(O)OR^5—$ and the $R^1$ group in ingredient D exhibits the formula $—R^7C(O)OR^5—$, where $R^7$ is $CH_2=C(R^{12})R^{7'}$. $R^7$ is selected from the same group as $R^4$, and $R^{7'}$ is selected from the same group of radicals as $R^{4'}$ or it can represent a single bond.

For the compounds of embodiment IV, the ethylenically unsaturated group represents the residue remaining following removal of the hydrogen atom from one hydroxyl group of the alcohol portion of an ester derived from reaction of a terminally unsaturated carboxylic acid with a saturated aliphatic or saturated cycloaliphatic alcohol containing at least two hydroxyl groups. Suitable saturated alcohols are discussed in connection with embodiment II.

The terminally unsaturated carboxylic acids used to prepare embodiment IV contain from 3 up to 20 or more carbon atoms. Representative members of this class include acrylic acid, 3-butenoic acid, 9-decenoic acid and 4-allylbenzoic acid.

The fifth type of ethylenically unsaturated group that can be bonded to the silicon atom of preferred embodiments of reactant D1 is derived from the ether of a saturated polyhydric alcohol and an ethylenically unsaturated monohydric alcohol. This group exhibits the formula $[CH_2=C(R^{12})R^{4'}O]_2R^8$— and the $R^1$ group in ingredient D exhibits the formula $[CH_2\ C(H)\ (R^{12})R^{4'}O]_2R^8$—. $R^{4'}$ and $R^{12}$ are as previously defined in this specification and $R^8$ is a trivalent hydrocarbon radical that preferably contains from 3 to 6 carbon atoms.

Suitable reactants for preparing ethers of this type are discussed in connection with other embodiments of reactant D1. In the formulae for the five embodiments of reactant D1, the radicals represented by $R^5$, $R^6$ and $R^8$ are bonded to the oxygen atom in formula 1.

Organosilicon compounds corresponding to any of the aforementioned five embodiments of reactant D1 can be prepared by reacting a silane of the general formula $X_{m+1}R^2_{3-m}Si$ with one of the terminally unsaturated, hydroxylated organic compounds described as precursors for embodiments I-V in the preceding paragraphs of this specification. The subsitutents represented by $R^4$, $R^5$, $R^6$ and $R^7$ are preferably unsubstituted alkylene radicals.

The reaction between the organic and organosilicon compounds used to prepare reactant D1 is conducted under conditions that are typical for condensation reactions of silanes containing hydrolyzable groups with hydroxylated organic compounds. These reactions are typically conducted under an inert, anhydrous atmosphere such as nitrogen at temperatures from ambient to 200° C. and may employ a catalyst. Useful catalysts include but are not limited to the titanium compounds described in a subsequent section of this specification. The hydrolyzable groups are preferably alkoxy or enoloxy.

The weight of catalyst typically constitutes from about 0.1 to about 5 percent of the combined weight of all reactants.

Reactions involving exchanges of the preferred silicon bonded alkoxy and enoloxy groups typically generate the alcohol or ketone corresponding to the original siliconbonded alkoxy or enoloxy group as a by-product. Because these reactions are often reversible, it is usually desirable to remove this by-product alcohol or ketone by distillation as the reaction progresses.

The course of exchange reactions involving the generation and removal of alcohol or other by-products can readily be followed by measuring the amount of by-product collected.

Methanol and ethanol are the lowest boiling alcohols, and it is therefore preferable that the hydrolyzable groups of reactant D1 be methoxy or ethoxy. For the same reason, when the hydrolyzable group is enoloxy it is preferably isopropenyloxy.

The reactants and catalyst used to prepare reactant D1 are heated for a period of time sufficient to achieve a substantially complete reaction, as indicated by the amount of alcohol or other by-product collected. This time period is typically from 1 to about 5 hours and the reaction mixture is preferably heated from about 50° to 200° C.

It may be desirable to include in the reaction mixture a liquid diluent that may also function as a solvent for the reactants. Suitable diluents include aliphatic and aromatic hydrocarbons that are liquid at ambient temperature and boil within the range of from 50° to about 250° C. Representative diluents include hexane, heptane and liquid aromatic hydrocarbons such as toluene and xylene.

Some of the ethylenically unsaturated organic reactants used to prepare reactant D1 will polymerize at the temperatures used to react them with the organosilicon compound. It may therefore be desirable to include in the reaction mixture an effective amount of a free radical scavenger such as hydroquinone to completely suppress or at least inhibit the tendency of the organic reactant to polymerize during preparation of the present compounds.

Those embodiments of reactant D1 that boil below about 200° C. under ambient or reduced pressure can be isolated by distilling the product from the reaction mixture. Higher boiling products can be isolated using known chromatographic techniques with gases or liquids as the carrier.

In some instances the reaction mixture in which the compound is prepared can be used directly as reactant D1 without isolation or purification.

In place of the group represented by $X_mR^2_{(3-m)}Si$, reactant D1 can contain a precursor that can be converted to this group following reaction with an organohydrogensiloxane (reactant D2). A preferred example of such a precursor group is the trimethylsiloxy group present in the silane $(CH_3)_3SiOCH_2CH=CH_2$. Following reaction of this silane with reactant D2 the trimethylsiloxy group is hydrolyzed to form a hydroxyl group. The hydroxyl group is then reacted with silane containing 3 or 4 alkoxy or other hydrolyzable groups such as ketoximo to obtain the desired $X_mR^2_{(3-m)}SiO$— group present in ingredient D, wherein X represents the hydrolyzable group.

Compounds wherein one of the $R^3$ substituents in formula I represents an alkenyl radical can be prepared by reacting compounds wherein $R^3$ is a silicon-bonded hydrogen atom with stoichiometric excess of a diene type hydrocarbon such as butadiene.

Reactant D2 can be any organosiloxane compound containing at least two silicon-bonded hydrogen atoms per molecule. This reactant contains from 2 to 20 or more silicon atoms per molecule, and the silicon-bonded hydrogen atoms can be located on terminal or non-terminal silicon atoms. This reactant provides the portion of the molecule represented by $[Si(R^3)_3]_n$ in formula 1.

Compounds suitable for use as reactant D2 include but are not limited to sym-tetramethyldisiloxane, sym-dimethyldiphenyldisiloxane, dimethylhydrogensiloxy-terminated polydimethylsiloxanes, dimethylhydrogensiloxy-terminated dimethylsiloxane/phenylmethylsiloxane copolymers, dimethylhydrogensiloxy-terminated dimethylsiloxane/diphenylsiloxane copolymers, dimethylhydrogensiloxy-terminated dimethylsiloxane/methyl-3,3,3-trifluoropropylsiloxane copolymers, trimethylsiloxy-terminated polymethylhydrogensiloxanes, trimethylsiloxy-terminated dimethylsiloxane/methylhydrogensiloxane copolymers and copolymers containing dimethylhydrogensiloxy and $SiO_{4/2}$ units.

A preferred embodiment of reactant D2 is a linear polydiorganosiloxane containing hydrogen atoms on the two terminal silicon atoms and can be represented by the general formula $H[(R^9)_2SiO]_qSiR^9_2H$, wherein q is at least 1 and all of the substituents represented by $R^9$ are monovalent hydrocarbon radicals. $R^9$ is preferably methyl, ethyl, phenyl or 3,3,3-trifluoropropyl, this preference being based on the availability of the intermediates used to prepare reactant D2, and q is preferably from 1 to 20.

The only restriction on the molecular weight of reactant D2 is that the liquid or solubilized form of this reactant be compatible with reactant D1.

The reaction between reactants D1 and D2 is a hydrosilation reaction and is typically conducted in the presence of a catalyst that is a metal from the platinum group of the periodic table or a compound of one of these metals.

Due to the exothermic nature of many hydrosilation reactions and the requirement to react only a portion of the silicon-bonded hydrogen atoms on reactant D2, it is usually preferable to gradually add the ethylenically unsaturated silane (reactant D1) to a stoichiometric excess of the organohydrogensiloxane (reactant D2). The molar ratio of D1:D2 is from 0.1:1 to 0.9:1, preferably from 0.5:1 to 0.8:1. It should be understood that higher relative molar concentrations of ingredient D2 are preferred when this ingredient contains more that two silicon-bonded hydrogen atoms per molecule.

To avoid excessive overheating and formation of undesirable by-products the temperature of the reaction mixture should be maintained below about 100° C., and preferably at about 70° C.

In accordance with a method for preparing a preferred class of novel compounds of the present invention an organohydrogensiloxane containing at least two silicon-bonded hydrogen atoms per molecule is reacted with an organosilicon compound of the formula $ZOR^{13}$ where Z represents the group $X_mR^2_{3-m}Si-$ or a precursor of this group, X represents a hydrolyzable group and $R^{13}$ represents an alkenyl radical wherein the unsaturated carbon atoms are located at a terminal position.

The reaction between preferred embodiments of a reactant D1 precursor and reactant D2 to form ingredient D is shown in the following general equations:

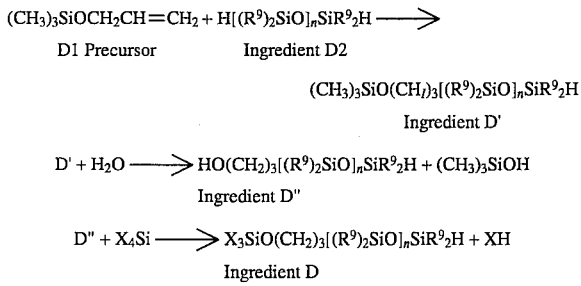

In the foregoing equations X preferably represents an alkoxy group containing from 1 to 4 carbon atoms, most preferably methoxy or ethoxy. Alternatively, X can represent a ketoximo group such as methylethylketoximo or other hydrolyzable group that will not interfere with the curing of organosiloxane compositions containing ingredient D as an adhesion promoting additive.

An alternative method for preparing ingredient D is by the reaction of a carbinol-functional silane or organosiloxane with a silane containing a group reactive with the carbinol group and a silicon-bonded hydrogen atom or alkenyl radical. This method is shown in the following equations:

$CH_3Si(OC_2H_5)_3$ + $HOC_2H_5(CH_3)_2SiO[Si(CH_3)_2O]_3SiO(CH_3)_2CH=CH_2$ ⟶

$CH_3(OC_2H_5)_2SiOC_2H_5Si(CH_3)_2O[Si(CH_3)_2O]_3SiO(CH_3)_2CH=CH_2$ + $C_2H_5OH$

Methods for preparing carbinol functional organosilicon compounds are described in the literature, for example in U.S. Pat. No. 5,290,901.

If the reaction product of the silane and the organohydrogensiloxane is subsequently reacted with a silane or siloxane containing at least two ethylenically unsaturated groups, referred to herein as reactant D3, one of the $R^9$ substituents in at least one of the $[SiR^9_pO_{3-p/2}]$ units is represented by the formula $-R^{11}[R^{10}_sSiO_{(3-s)/2}]_r$. In this formula $R^{11}$ represents the alkylene radical resulting from reaction of an ethylenically unsaturated group with a silicon-bonded hydrogen atom, each $R^{10}$ is individually selected from the group consisting of unsubstituted and substituted monovalent hydrocarbon radicals and hydrolyzable groups represented by X, r is at least 1 and the value of s is individually selected from 0, 1, 2 and 3 in each unit.

The saturated monovalent hydrocarbon radicals are alkyl, most preferably methyl and one of the $R^{10}$ radicals in one or more of the siloxane units represents an ethylenically unsaturated hydrocarbon radical or an ethylenically unsaturated group such as acryloxypropyl or methacryloxypropyl. $R^{11}$ preferably contains the same number and configuration of carbon atoms as the unsaturated group represented by $R^{10}$. The unsaturated hydrocarbon radical is preferably vinyl or allyl and $R^{11}$ is preferably ethylene or propylene.

In preferred embodiments of reactant D3 the unsaturated groups are vinyl, allyl, 5-hexenyl or 3-methacryloxypropyl. Reactant D3 is preferably sym-tetramethyldivinyldisiloxane.

The reaction between (1) the reaction product of reactants D1 and D2 and (2) reactant D3 is carried out under conditions similar to those used for the reaction of reactants D1 and D2. In this instance reaction product (1) is gradually added to a stoichiometric excess of reactant D3.

The purity of the reaction product can be increased by the choice of catalyst and the stoichiometric ratio of alkoxysilane to organohydrogensiloxane.

Curable compositions suitable for use with the present adhesion-promoting organosiloxane compositions as adhesion promoters can cure by any of the reactions known for curing organosiloxane compositions, with the exception of the reaction of silanol groups with silicon-bonded hydrolyzable groups that occurs in the presence of moisture. The curing reactions that can be used in the presence of the adhesion-promoting compositions of this invention include hydrosilation reactions catalyzed by platinum group metals and compounds thereof, the reaction of silicon-bonded hydrogen atoms with silanol groups, the reaction of mercapto groups with one another in the presence of oxygen and a catalyst, the reaction of mercapto groups with alkenyl radicals in the presence of a catalyst, free radical and cationic reactions initiated by irradiation of photosensitive compounds with ultraviolet light, free radical reactions initiated by the thermally induced decomposition of a free radical precursor and reactions initiated by high energy radiation.

As used in this specification the term "cure" means the conversion of a liquid or semi-solid composition to a crosslinked elastomeric or resinous material by the reaction of groups present on the polyorganosiloxane referred to as ingredient A of the present compositions with the curing agent.

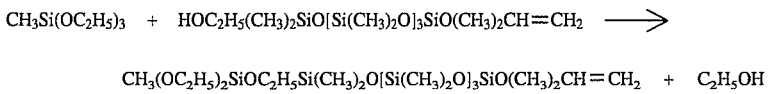

The present inventors discovered that the compounds of this invention are particularly suitable for use with organosiloxane compositions that cure by a platinum-catalyzed hydrosilation reaction when the compounds are present in the curable composition.

Unlike many of the known adhesion promoters for organosiloxane compositions, the present organosiloxane compounds are effective at curing temperatures from ambient to about 70° C.

To develop the cohesive bonding to a variety of substrates during curing of the present compositions, the concentration of ingredient D should be equivalent to from 0.2 to about 10 weight percent, based on the weight of the entire curable composition, preferably from 0.5 to 2.5 weight percent.

The required and optional ingredients of preferred and alternative curable organosiloxane compositions suitable for use with the adhesion-promoting additives of the present invention will now be explained in detail.

The Curable Polyorganosiloxane (Ingredient A)

An alkenyl-containing polyorganosiloxane, referred to hereinafter as ingredient A, present in organosiloxane compositions that cure by a hydrosilation reaction is the principal ingredient of preferred curable compositions suitable for use with the present adhesion-promoting additives.

To achieve curing of these compositions the preferred embodiment of ingredient A contains at least two silicon-bonded alkenyl radicals in each molecule.

Suitable alkenyl radicals contain from 1 to about 10 carbon atoms and are exemplified by but not limited to vinyl, allyl and 5-hexenyl. The silicon-bonded organic groups other than alkenyl radicals present in ingredient A are typically monovalent hydrocarbon and halogenated monovalent hydrocarbon radicals exemplified by but not limited to alkyl radicals such as methyl, ethyl and propyl; aryl radicals such as phenyl; and halogenated alkyl radicals such as 3,3,3-trifluoropropyl.

The molecular structure of ingredient A is not critical to the present invention, and will be determined by the physical properties desired in the cured composition. To achieve a useful level of tensile properties in the elastomers and other products prepared by curing the present compositions, the molecular weight of this ingredient should be sufficient to achieve a viscosity at 25° C. greater than about 0.1 Pa.s.

The upper limit for the molecular weight of ingredient A is not specifically restricted, and is typically limited only by the processability of the curable organosiloxane composition. The polyorganosiloxanes range from pourable liquids to gum type polymers that are typically characterized by Williams plasticity values.

Preferred embodiments of ingredient A are polydiorganosiloxanes represented by the general formula 2

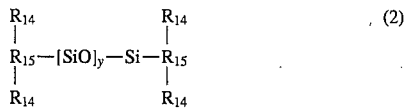

wherein each $R^{14}$ is individually selected from monovalent hydrocarbon radicals, $R^{15}$ represents a vinyl or other alkenyl radical, and X represents a degree of polymerization equivalent to a viscosity of at least 100 centipoise (0.1 Pa.s), preferably from 0.1 to 10 Pa.s.

As used in the present specification, monovalent hydrocarbon radicals include but are not limited to alkyl containing from 1 to about 20 carbon atoms, such as methyl, ethyl, n-hexyl and n-dodecyl; alkenyl such as vinyl and allyl; cycloalkyl such as cyclohexyl; aryl radicals such as phenyl and naphthyl; aralkyl such as benzyl and alkaryl such as tolyl and xylyl.

The hydrocarbon radicals represented by $R^{14}$ are either unsubstituted or can contain substituents such as halogen atoms that will not adversely affect the storage stability and curing of the present compositions or the properties of cured articles prepared from these compositions.

The two $R^{14}$ substituents on each of the silicon atoms in formula I can be identical or different, and can contain from 1 to about 20 carbon atoms. A range of from 1 to 10 carbon atoms is preferred based on the availability of the corresponding monomers. Most preferably at least one of the hydrocarbon radicals on each silicon atom is methyl, and any remainder are vinyl, phenyl and/or 3,3,3-trifluoropropyl, this preference being based on the availability of the reactants typically used to prepare the polydiorganosiloxane and the properties of cured elastomers prepared from these polydiorganosiloxanes. For the same reasons, $R^{15}$ is preferably vinyl or 5-hexenyl.

Representative embodiments of ingredient A containing ethylenically unsaturated hydrocarbon radicals only at the terminal positions include but are not limited to dimethylvinylsiloxy-terminated polydimethylsiloxanes, dimethylvinylsiloxy-terminated polymethyl-3,3,3-trifluoropropylsiloxanes, dimethylvinylsiloxy-terminated -dimethylsiloxane/3,3,3-trifluoropropylmethylsiloxane copolymers and dimethylvinylsiloxy-terminated dimethylsiloxane/methylphenylsiloxane copolymers.

Methods for preparing ingredient A of the present compositions by hydrolysis and condensation of the corresponding halosilanes or by condensation of the cyclic polydiorganosiloxanes are sufficiently disclosed in the patent and other literature that a detailed description in this specification is not necessary.

For applications requiring high levels of physical properties such as tear strength it may be desirable to include in the curable organosiloxane composition a second polydiorganosiloxane containing ethylenically unsaturated hydrocarbon radicals bonded to both terminal and non-terminal silicon atoms.

The Organohydrogensiloxane Curing Agent (Ingredient B)

The preferred curable organosiloxane compositions of this invention contain at least one organohydrogensiloxane that functions as a curing agent for ingredient A. In the presence of the hydrosilation catalyst, referred to as ingredient C, the silicon-bonded hydrogen atoms in ingredient B undergo an addition reaction, referred to as hydrosilation, with the silicon-bonded alkenyl groups in ingredient A, resulting in crosslinking and curing of the composition.

Ingredient B must contain at least 2 silicon-bonded hydrogen atoms in each molecule. If ingredient A contains only two alkenyl radicals per molecule, ingredient B must contain an average of more than two silicon-bonded hydrogen atoms to achieve a crosslinked structure in the final cured product.

The silicon-bonded organic groups present in ingredient B are selected from the same group of monovalent hydrocarbon and halogenated hydrocarbon radicals as the organic groups of ingredient A. The organic groups in ingredient B are preferably substantially free of ethylenic or acetylenic unsaturation. The molecular structure of ingredient B can be straight chain, branch-containing straight chain, cyclic, or network.

While the molecular weight of ingredient B is not specifically restricted, viscosities in the range of 3 to 10,000 centipoise (0.003 to 10 Pa.s) at 25 degrees Centigrade are preferred.

The concentration of ingredient B is sufficient to provide a molar ratio of silicon-bonded hydrogen atoms to alkenyl radicals in the curable composition of from 0.5 to 20. A range of from 0.5 to 2 is preferred.

When the curable composition contains less than 0.5 moles of silicon-bonded hydrogen atoms per mole of alkenyl radicals it may not be possible to achieve the desired physical properties following curing. The physical properties of the cured article may vary with time when this ratio exceeds about 20 moles of silicon-bonded hydrogen per mole of alkenyl radicals.

The Platinum-Containing Hydrosilation Reaction Catalyst (IngredientC)

Curing of the present compositions is catalyzed by a hydrosilation catalyst that is a metal from the platinum group of the periodic table or a compound of such a metal. These metals include platinum, palladium and rhodium. Platinum and platinum compounds are preferred based on the high activity level of these catalysts in hydrosilation reactions.

Examples of preferred curing catalysts include but are not limited to platinum black, platinum metal on various solid supports, chloroplatinic acid, alcohol solutions of chloroplatinic acid, and complexes of chloroplatinic acid with liquid ethylenically unsaturated compounds such as olefins and organosiloxanes containing ethylenically unsaturated hydrocarbon radicals bonded to silicon. Complexes of chloroplatinic acid with the aforementioned organosiloxanes containing ethylenically unsaturated hydrocarbon radicals are described in U.S. Pat. No. 3,419,593, which issued to David N. Willing on Dec. 31, 1968. The relevant portions of this patent are incorporated herein by reference as a teaching of preferred catalysts.

The concentration of ingredient C in the present compositions is equivalent to a platinum concentration of from 0.1 to 500 parts by weight of platinum metal, preferably from 1 to 50 parts by weight of platinum metal, per million parts (ppm), based on the combined weight of ingredients A and B.

Curing does not proceed[satisfactorily at below 0.1 ppm of platinum, while using more than 500 ppm results in no appreciable increase in cure rate, and is therefore uneconomical.

Platinum Catalyst Inhibitor

Mixtures of the aforementioned ingredients A, B and C may begin to cure at ambient temperature. To obtain a longer working time or "pot life", the activity of the catalyst under ambient conditions can be retarded or suppressed by addition of a suitable inhibitor.

Known platinum catalyst; inhibitors include the acetylenic compounds disclosed in U.S. Pat. No. 3,445,420, which issued on May 20, 1969 to Kookootsedes et al. Acetylenic alcohols such as 2-methyl-3-butyn-2-ol constitute a preferred class of inhibitors that will suppress the activity of a platinum-containing catalyst at 25° C. Compositions containing these catalyst inhibitors typically require heating at temperatures of 70° C. or above to cure at a practical rate.

When it is desired to increase the pot life of a curable composition under ambient conditions, this can be accomplished using an alkenyl substituted siloxane of the type described in U.S. Pat. No. 3,989,667, which issued on Nov. 2, 1976 to Lee and Marko. Cyclic methylvinylsiloxanes are preferred.

Inhibitor concentrations as low as one mole of inhibitor per mole of platinum will in some instances impart satisfactory storage stability and cure rate. In other instances inhibitor concentrations of up to 500 or more moles of inhibitor per mole of platinum are required. The optimum concentration for a given inhibitor in a given composition can readily be determined by routine experimentation and does not constitute part of this invention.

Optional Ingredients
Reinforcing Fillers

To achieve high levels of tear strength and other physical properties that characterize some types of cured elastomers that can be prepared using the compositions of this invention, it may be desirable to include a reinforcing filler such as finely divided silica. Silica and other reinforcing fillers are often treated with one of more of the known filler treating agents to prevent a phenomenon referred to as "creping" or "crepe hardening" during processing of the curable composition.

Finely divided forms of silica are preferred reinforcing fillers. Fumed silicas are particularly preferred because of their relatively high surface area, which is typically at least 50 square meters per gram. Fillers having surface areas of at least 200 square meters per gram are preferred for use in the present method.

The amount of finely divided silica or other reinforcing filler used in the present compositions is at least in part determined by the physical properties desired in the cured elastomer. Liquid or pumpable polyorganosiloxane compositions typically contain from about 10 to about 60 percent by weight of silica, based on the weight of polydiorganosiloxane. This value is preferably from about 30 to about 50 percent.

The filler treating agent can be any of the low molecular weight organosilicon compounds disclosed in the art as being suitable for preventing creping of organosiloxane compositions during processing. The treating agents are typically liquid hydroxyl terminated polydiorganosiloxanes containing an average of from 2 to about 20 repeating units per molecule, and organosilicon compounds such as hexaorganodisiloxanes and hexaorganodisilazanes that hydrolyze and condense under the conditions used to treat the filler. Preferably at least a portion of the silicon bonded hydrocarbon radicals present on the treating agent are identical to a majority of the hydrocarbon radicals present in ingredients A and B. A small amount of water can be added together with the silica treating agent(s) as a processing aid.

It is believed that the treating agents function by reacting with silicon-bonded hydroxyl groups present on the surface of the silica or other filler particles to reduce interaction between these particles and the polyorganosiloxanes present in the curable composition.

When a silica filler is used, it is preferably treated in the presence of at least a portion of the other ingredients of the present compositions by blending these ingredients together until the filler is completely treated and uniformly dispersed to form a homogeneous material.

The ingredients that are present during treatment of the filler typically include the silica treating agents and at least a portion of the polydiorganosiloxane(s) referred to herein as ingredient A.

Additional Optional Ingredients

The present organosiloxane compositions can contain one or more additives that are conventionally present in curable compositions of this type to impart or enhance certain physical properties of the cured composition in addition to adhesion or to facilitate processing of the curable composition.

Typical additives include but are not limited to non-reinforcing fillers such as quartz, alumina, mica and calcium carbonate; pigments such as carbon black and titanium dioxide; dyes, flame retardants, and heat and/or ultraviolet light stabilizers. Resinous organosiloxane copolymers can be used in place of or in combination with one or more reinforcing fillers to improve the physical properties of the cured organosiloxane composition.

A preferred type of resinous copolymer contains repeating units of the general formula $SiO_{4/2}$ in addition to triorganosiloxy units of the general formulae $R^{16}_3SiO_{1/2}$ and diorganovinylsiloxy units of the general formula $CH_2=CH(R^{17})_2SiO_{1/2}$. In these formulae $R^{16}$ and $R^{17}$ are individually monovalent hydrocarbon or substituted monovalent hydrocarbon radicals as previously defined for the $R^{15}$ radicals of ingredient A.

The molar ratio of the combination of triorganosiloxy units and diorganovinylsiloxy units to $SiO_{4/2}$ units in the resinous copolymer is from 0.7 to 1.2, inclusive. The vinyl-containing units constitute from 2 to 8 percent by weight of the copolymer, which preferably contains at least two vinyl radicals per molecule. In preferred embodiments of the copolymer the ranges for the molar ratio of diorganovinylsiloxy: triorganosiloxy: $SiO_{4/2}$ units is 0.08–0.1:0.06–1:1.

The resinous copolymers can be prepared as described in U.S. Pat. No. 2,676,182, which issued to Daudt and Tyler on Apr. 20, 1954 and is hereby incorporated in this specification by reference thereto to teach the preparation of and the scope of these resins. The copolymers described in this patent contain from 2 to 23 percent by weight of hydroxyl groups, which is considerably above the maximum level of about 0.8 weight percent preferred for precursors of the present copolymers. The hydroxyl content of the precursor can be conveniently reduced to the desired level by employing a higher concentration of triorganosiloxy units than the concentration range taught by Daudt et al.

Alternative Curable Organosiloxane Compositions

In place of the polyorganosiloxanes, curing agents and catalysts referred to in the preceding section of this specification as ingredients A, B and C, the present adhesion promoting additives can be used with organosiloxane compositions that cure by other types of reactions. These reactions include but are not limited to the reaction of silicon-bonded hydrogen atoms with silanol groups, the reaction of mercapto groups with one another in the presence of oxygen and a catalyst, the reaction of mercapto groups with alkenyl radicals in the presence of a catalyst, free radical and cationic reactions initiated by irradiation of photosensitive compounds with ultraviolet light, free radical reactions initiated by the thermally induced decomposition of a free radical precursor and reactions initiated by high energy radiation.

Preparation of Curable Compositions

The compositions of this invention can be prepared by combining all of ingredients at ambient temperature. Any of the mixing techniques and devices described in the prior art can be used for this purpose. The particular device used will be determined by the viscosity of the ingredients and the final curable composition. Suitable mixers include but are not limited to paddle type mixers, kneader type mixers and two- and three-roll rubber mills.

Cooling of the ingredients during mixing may be desirable to avoid premature curing of the composition.

To maximize storage stability preferred curable organosiloxane compositions that cure by a hydrosilation reaction, these compositions are preferably kept in closed containers until used. If greater storage stability is desired, the compositions can be packaged in two or more containers with the organohydrogensiloxane (ingredient B) and the platinum group metal catalyst (ingredient C) in separate containers.

Depending upon the types and concentrations of ingredients A and B, cured organosiloxane materials prepared using the present compositions can vary in properties from brittle resins to elastomers to gels, and are useful in a variety of end-use applications as coatings or as molded or extruded articles. Unfilled materials are particularly useful as adhesives, protective coatings, encapsulants and potting compositions for protecting delicate electronic devices such as transistors and integrated circuits from damage by moisture and other materials present in the environment that can adversely affect operation of the device. The compositions can be used to coat either the individual devices or a circuit board containing a number of these devices together with other electronic components.

The present compositions can be applied to substrates by spraying, dipping, pouring, extrusion or by the use of a brush, roller or coating bar. The selection of a particular application method will be determined at least in part by the viscosity of the curable composition. The viscosity of the composition can be reduced using suitable solvents or reactive diluents as known in the art.

Organosiloxane compositions containing the present adhesion additives cohesively bond to a variety of organic and inorganic substrates during curing at temperatures as low as 25° C. The ability of the present compositions to develop adhesion when cured at these relatively low temperatures make them suitable for application to substrates that cannot withstand the elevated temperatures of 100° C. or higher required to cure organosiloxane compositions containing prior art adhesion additives, some of which may inhibit platinum group metal catalysts.

Preferred compositions cure over a period of several hours under ambient conditions. As is true for other compositions that cure by a platinum-catalyzed hydrosilation reaction, curing can be accelerated by heating. Curing temperatures of from 25° to about 80° C. are preferred.

EXAMPLES

The following examples describe preferred curable compositions of the present invention and should not be interpreted as limiting the scope of the invention defined in the accompanying claims. Unless otherwise specified all parts and percentages in the example are by weight and viscosities were measured at 25° C.

Example 1

Preparation of $(C_2H_5O)_3SiO(CH_2)_3Si(CH_3)_2OSi(CH_3)_2H$

Allyloxytrimethylsilane was prepared by charging a glass reactor with 100.1 g of allyl alcohol and 140.1 g of hexamethyldisilazane (HMDZ). The reactor was equipped with a water-cooled condenser and a nitrogen inlet. The contents of the reactor were heated at the boiling point for 4 hours under a nitrogen atmosphere, at which time 20.0 g. of additional HMDZ were added. Heating of the reaction mixture at the boiling point was continued for an additional 3 hours. Analysis of the reaction mixture indicated the substantial absence of unreacted allyl alcohol and a small amount of unreacted HMDZ.

A reactor was charged with 259.1 g. of sym-tetramethyldisiloxane and 30 microliters of a 0.02 molar solution of hexachloroplatinic acid solution in isopropyl alcohol. The reactor was equipped with a water-cooled condenser, stirring means and an addition funnel containing 100.1 g. of the allyloxytrimethylsilane prepared as described in the preceding paragraph of this example. The contents of the reactor were heated to 70° C., at which time addition of the silane was begun. The temperature of the reaction mixture was maintained at about 70° C. during the addition. Following completion of the addition the reaction mixture was heated within the range from 77° to 110° C. for one hour. Unreacted tetramethyldisiloxane was removed during this heating period.

Distillation of the reaction mixture yielded 69 g. of 95% pure Me$_3$SiO(CH$_2$)$_3$SiMe$_2$OSiMe$_2$H (I), where Me represents the methyl radical. Hydrolysis of the trimethylsiloxy group of this product was achieved by reacting 35 g. of the product with 35 g. of methanol and 1 drop of concentrated (37 weight percent) hydrochloric acid under ambient conditions for about 18 hours. Volatile materials were then removed under reduced pressure at a temperature of 38° C. to yield HO(CH$_2$)$_3$SiMe$_2$OSiMe$_2$H (II).

The final product (ingredient D) was prepared by charging a reactor with 16.5 g. of tetraethyl orthosilicate and 0.25 g. of tetrabutyltitanate. The reactor was equipped with a distillation head, water-cooled condenser, a receiver cooled using "dry" ice and an addition funnel containing 15.23 g. of II. The contents of the reactor were heated to 75° C. while being maintained under a nitrogen atmosphere, at which time addition of II was begun. The addition required 23 minutes. Following completion of the addition the temperature of the reaction mixture was increased sufficiently to remove the ethanol formed as a by-product of the reaction together with unreacted tetraethyl orthosilicate. 4.75 g. of liquid were collected. The product, a mixture of compounds exhibiting the general formula (C$_2$H$_5$O)$_x$Si[O(CH$_2$)$_3$Si(CH$_3$)$_2$OSi(CH$_3$)$_2$H]$_{4-x}$ and a small amount of unreacted tetraethyl orthosilicate, remained as a residue in the reactor. The major reaction product was the compound in which x in the general formula is 3.

Example 2

Preparation of (C$_2$H$_5$O)$_3$SiO(CH$_2$)$_3$Si(CH$_3$)$_2$OSi(CH$_3$)$_2$(CH$_2$)$_2$Si(CH$_3$)$_2$OSi(CH$_3$)$_2$CH=CH$_2$ A reactor equipped with a water cooled condenser and an addition funnel was charged with 176.2 g. of sym-tetramethyldivinyldisiloxane and 460 microliters of a 0.02 molar solution of hexachloroplatinic acid solution in isopropyl alcohol. 24.7 g. of the intermediate product of Example 1 (identified as I) were placed in the addition funnel. The contents of the reactor were heated to 80° C., at which time the contents of the addition funnel were added over a period of about 1 hour, during which time the temperature of the reaction mixture was maintained between 82 and 89° C. Following completion of the addition the temperature of the reaction mixture was increased to 138° C. and maintained at this level for about 8 hours, at which time none of compound I could be detected using gas-liquid chromatography. Unreacted disiloxane was then removed by distillation to obtain

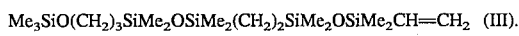

Me$_3$SiO(CH$_2$)$_3$SiMe$_2$OSiMe$_2$(CH$_2$)$_2$SiMe$_2$OSiMe$_2$CH=CH$_2$ (III).

24.77 g. of this product together with 30.95 g. of methanol and 1 drop of concentrated (37 weight percent) hydrochloric acid were placed in a reactor and stirred for about 16 hours under ambient conditions, at which time volatile products were removed under reduced pressure and ambient temperature. The residue in the reactor will be referred to as material IV, and was believed to be HO(CH$_2$)$_3$SiMe$_2$OSiMe$_2$(CH$_2$)$_2$SiMe$_2$OSiMe$_2$CH=CH$_2$.

The desired final product was prepared by charging a reactor with 8.12 g. of tetraethyl orthosilicate and 0.2 g. of tetrabutyl titanate. The reactor was equipped with a distillation head and an addition funnel containing 17.21 g. of the material IV. The contents of the reactor were heated to 75° C. while the contents of the addition funnel were added over a 45 minute period. Following completion of the addition the reaction mixture was heated sufficiently to remove 1.02 g. of volatile material by distillation. Analysis by gas-liquid chromatography indicated that the residue in the reactor contained unreacted tetraethyl orthosilicate and a number of different reaction adducts, including at least one compound of the present invention as the major product.

Example 3

This example demonstrates the adhesion to a variety of substrates that can be achieved using the compounds of the present invention as adhesion promoters.

The two part curable organosiloxane composition used to evaluate the adhesion promoters contained the following ingredients:

Part A:

46 parts of a dimethylvinylsiloxy-terminated polydimethylsiloxane having a viscosity of about 0.4 Pa.s at 25° C. 46 parts of quartz having an average particle size of 5 microns; 7 parts of a dispersion containing 80 weight percent of a dimethylvinylsiloxy-terminated polydimethylsiloxane having a viscosity of about 0.4 Pa.s at 25° C., 13 weight percent zinc oxide and 7 weight percent lampblack; and 0.2 part of a reaction product of hexachloroplatinic acid and sym-tetramethyldivinyldisiloxane that has been diluted with a liquid dimethylvinylsiloxy terminated polydimethylsiloxane in an amount sufficient to achieve a platinum content of 0.7 weight percent.

Part B 47 parts of a dimethylvinylsiloxy-terminated polydimethylsiloxane exhibiting a viscosity of about 0.4 Pa.s at 25° C. (Ingredient A) 47 parts of quartz having an average particle size of 5 microns;

6 parts of a trimethylsiloxy-terminated polydiorganosiloxane containing an average of five methylhydrogensiloxane units and three dimethylsiloxane units per molecule with a silicon-bonded hydrogen atom content in the range from about 0.7 to 0.8 weight percent (Ingredient B), and 0.1 part of cyclic methylvinylsiloxanes.

Some of the compositions contained additional quantities of the organohydrogensiloxane.

The amounts of parts A and B of the curable composition and the type and amounts of adhesion promoter used to prepare each of the compositions evaluated are summarized in Table 1. All of the compositions contained 0.01 part of tetrabutyl titanate. Two of the compositions contained additional amounts of the same organohydrogensiloxane (ingredient B) present in the part A of the curable composition.

TABLE 1

| Ingredient | Composition | | | |
|---|---|---|---|---|
| (parts) | 1 | 2 | 3 | 4 |
| Part A | 4.90 | 4.75 | 4.88 | 4.69 |
| Part B | 4.90 | 4.75 | 4.90 | 4.70 |
| Adhesion Additive | | | | |
| Example | 1 | 1 | 2 | 2 |
| Parts | 0.25 | 0.52 | 0.28 | 0.51 |
| Ingredient B | 0 | 0 | 0.07 | 0.12 |

Portions of each of the four compositions were coated as 0.008-inch (0.2 mm.)-thick films on the following substrates using a draw-down bar: glass microscope slides, mill finish aluminum panels containing an alloy coating and available as type 3003 H14 Q panels from Q-Panel Company; bare aluminum panels available as type 2024 bare aluminum Q panels from Q-panel Company; an epoxy-fiberglass laminate available as FR4 boards from Kepro Circuit Systems; and copper panels.

Each of the compositions evaluated was cured on each of the substrates at room temperature and for 30 minutes at 70° C. The coatings cured at room temperature were evaluated 1, 3 and 7 days after being coated and the coatings cured at 70° C. for 30 minutes were evaluated immediately after cooling following removal from the oven and after 1, 3, and 7 days of additional curing at room temperature.

The adhesion test consisted of scratching the cured coatings with the blade of a metal spatula to determine whether the coating could be removed without leaving a residue on the surface (adhesive failure) or whether failure occurred within the coating layer, resulting in at least a portion of the coating material in the test area adhering to the substrate (cohesive failure).

Coatings exhibiting cohesive failure were further tested to determine if the residue on the substrate and the adjacent coating material could be removed by rubbing with a finger. If the coating could be removed in this manner, the pressure required to remove the coating was rated on a subjective scale as slight (WE), medium (WM) or high (WD).

The results of the adhesion tests are summarized in Table 2.

TABLE 2

| Comp. | Cure Temp. | Time* | Glass | Bare Al | Milled Al | Copper | Epoxy |
|---|---|---|---|---|---|---|---|
| 1 | RT | 1 day | CF | AF | CF | CF | CF |
|   |    | 3 days | CF | CF | CF | CF | CF |
|   |    | 7 days | CF | CF | CF | CF | CF |
| 1 | 70° C. | 30 min. | AF | AF | AF | AF | AF |
|   |        | 1 day | WM | WD | AF | WD | AF |
|   |        | 3 days | CF | CF | CF | CF | WE |
|   |        | 7 days | CF | CF | CF | CF | CF |
| 2 | RT | 1 day | CF | CF | CF | CF | CF |
|   |    | 3 days | CF | CF | CF | CF | CF |
|   |    | 7 days | CF | CF | CF | CF | CF |
| 2 | 70° C. | 30 min. | AF | AF | AF | AF | AF |
|   |        | 1 day | AF | AF | AF | WD | AF |
|   |        | 3 days | WM | WE | CF | AF | AF |
|   |        | 7 days | CF | CF | CF | CF | AF |
| 3 | RT | 1 day | CF | AF | CF | AF | AF |
|   |    | 3 days | CF | WD | CF | AF | AF |
|   |    | 7 days | CF | CF | CF | CF | AF |
| 3 | 70° C. | 30 min. | CF | AF | AF | AF | AF |
|   |        | 1 day | CF | AF | CF | AF | AF |
|   |        | 3 days | CF | AF | CF | AF | AF |
|   |        | 7 days | CF | CF | CF | CF | WE |
| 4 | RT | 1 day | CF | CF | CF | CF | CF |
|   |    | 3 days | CF | CF | CF | CF | CF |
|   |    | 7 days | CF | CF | CF | CF | CF |
| 4 | 70° C. | 30 min. | CF | AF | WE | AF | AF |
|   |        | 1 day | CF | WE | CF | AF | CF |
|   |        | 3 days | CF | CF | CF | CF | CF |
|   |        | 7 days | CF | CF | CF | CF | CF |

* = Time interval following application of coating

The data in Table 2 demonstrate the ability of compositions containing the present compounds to develop adhesion to a variety of substrates during curing of the compositions at room temperature. Compositions containing 5 weight percent of the adhesion promoters exhibited cohesive failure to all five substrates evaluated after curing for one day. Compositions containing the lower level of adhesion promoter achieved cohesive failure within seven days.

That which is claimed is:

1. An organosiloxane compound represented by the formula $$X_m R^2_{(3-m)} SiOR^1 [Si(R^3)_3]_n$$

wherein $R^1$ contains at least 3 carbon atoms, exhibits a valence of n+1 wherein n is 1 or 2, and is selected from the group consisting of $—R^4—$, $—R^4OR^5—$, $—R^4OC(O)R^6—$ and $—R^7C(O)OR^5—$ when n is 1 and $R^1$ is $(—R^4O)_2R^8—$ when n is 2 and wherein $R^5$, $R^6$ and $R^8$ are bonded to the oxygen atom in said formula;

$R^4$ represents a hydrocarbylene or substituted hydrocarbylene radical containing at least 3 carbon atoms wherein the substituent is hydroxyl or alkoxy;

$R^5$ contains from 2 to 12 carbon atoms and is selected from the group consisting of hydrocarbylene radicals and allyloxy-substituted hydrocarbylene radicals;

$R^6$ represents a hydrocarbylene or substituted hydrocarbylene radical containing at least 3 carbon atoms wherein the substituent is hydroxyl or alkoxy;

$R^7$ is selected from the group consisting of $R^6$ and a single bond;

$R^8$ represents a trivalent hydrocarbon radical;

each $R^2$ is individually selected from the group consisting of unsubstituted monovalent hydrocarbon radicals and substituted monovalent hydrocarbon radicals;

each $R^3$ is individually selected from the group consisting of unsubstituted and substituted monovalent hydrocarbon radicals, silicon bonded hydrogen atoms, X and siloxane units represented by the general formula $—O[SiR^9_p O_{(3-p)/2}]_q$ wherein q is at least 1 and said siloxane units are sequential when q is greater than 1;

each $R^9$ is individually selected from the group consisting of X, hydrogen, substituted and unsubstituted monovalent hydrocarbon radicals, $X_m R^2_{3-m} SiOR^1—$ and $—R^{11}[R^{10}_s SiO_{(3-s)/2}]_r$ wherein r is at least 1 and the siloxane units represented by $R^{10}_s SiO_{(3-s)/2}$ are sequential when r is greater than 1, with the proviso that at least one substituent represented by $R^3$ contains a silicon-bonded hydrogen atom or alkenyl radical;

each $R^{10}$ is individually selected from the group consisting of monovalent hydrocarbon radicals, hydrogen and X;

$R^{11}$ represents a hydrocarbylene or substituted hydrocarbylene radical containing at least 2 carbon atoms wherein the substituent is hydroxyl or alkoxy;

the substituents present on the substituted hydrocarbon radicals represented by $R^2$, $R^3$, $R^9$, $R^{10}$ and $R^{11}$ are selected from the group consisting of halogen, epoxy, amino, mercapto and 3-methacryloxypropyl;

X represents a hydrolyzable group;

m is 2 or 3;

n is 1 or 2;

p is 0, 1, 2 or 3; and s is 0, 1, 2, or 3.

2. A compound according to claim 1 wherein $R^1$ contains from 3 to 10 carbon atoms;

at least one $R^3$ substituent is $—O[SiR^9_p O_{(3-p)/2}]_q$ wherein at least one of the $R^9$ substituents in said compound represents hydrogen;

all unsubstituted and substituted monovalent hydrocarbon radicals other than alkenyl radicals containing from 1 to 20 carbon atoms;

$R^4$, $R^5$, $R^6$ and $R^7$ represent identical or different unsubstituted alkylene radicals;

$R^8$ contains from 3 to 6 carbon atoms; and

X is alkoxy or ketoximo.

3. A compound according to claim 2 wherein the monovalent hydrocarbon radicals other than alkenyl present in said compound are selected from the group consisting of alkyl radicals containing from 1 to 4 carbon atoms, phenyl, and 3,3,3-trifluoropropyl;

$R^4$ and $R^6$ contain from 3 to 12 carbon atoms;

$R^5$ contains from 2 to 12 carbon atoms;

at least one of the siloxane units represented by the formula $[SiR^9_p O_{(3-p)/2}]$ is a diorganohydrogensiloxane unit, any remaining units include at least one member selected from the group consisting of diorganosiloxane units and organohydrogensiloxane units; and X is alkoxy containing from 1 to 4 carbon atoms.

4. A compound according to claim 1 wherein $R^1$ contains from 3 to 10 carbon atoms;

at least one $R^3$ substituent is $-O[SiR^9_p O_{(3-p)/2}]_q$ wherein at least one of the $R^9$ substituents in said compound represents $-R^{11}[SiR^{10}_s O_{(3-s)/2}]_r$;

$R^4, R^5, R^6$ and $R^7$ are individually selected from the group consisting of unsubstituted alkylene radicals;

$R^8$ contains from 3 to 6 carbon atoms; and

X is alkoxy containing from 1 to 4 carbon atoms.

5. A compound according to claim 4 wherein the monovalent hydrocarbon radicals other than alkenyl present in said compound are selected from the group consisting of alkyl radicals containing from 1 to 4 carbon atoms, phenyl, and 3,3,3-trifluoropropyl; and wherein one of the three $R^{10}$ groups bonded to the terminal silicon atom is an alkenyl radical containing from 2 to 10 carbon atoms.

6. A compound according to claim 5 wherein at least one of the substituents represented by $R^9$ is $-R^{11}Si(R^{10})_2OSiR^{10}_3$, said $R^{10}$ alkenyl radical is selected from the group consisting of vinyl, allyl, butenyl and 5-hexenyl, and the remaining $R^{10}$ groups are alkyl radicals containing from 1 to 4 carbon atoms.

7. A compound according to claim 6 wherein at least one of the monovalent hydrocarbon radicals bonded to each silicon atom containing these monovalent hydrocarbon radicals is methyl.

\* \* \* \* \*